US00PP10182P

United States Patent [19]

Zerr

[11] Patent Number: Plant 10,182

[45] Date of Patent: Jan. 6, 1998

[54] POINTSETTIA PLANT NAMED 'FISSONOSA'

[75] Inventor: Katharina Zerr, Simmern, Germany

[73] Assignee: Florfis AS, Binningen, Switzerland

[21] Appl. No.: 598,622

[22] Filed: Feb. 12, 1996

[51] Int. Cl.[6] ..... A01H 5/00

[52] U.S. Cl. ..... Plt./86.3

[58] Field of Search ..... Plt./86.1, 86.3

[56] References Cited

PUBLICATIONS

LIPOVROM Plant Variety Database 1996/02 citation PBR ELLP00168 of Dec. 23, 1994 for 'Fissonosa'.

*Primary Examiner*—James R. Feyrer

*Attorney, Agent, or Firm*—Foley & Lardner

[57] ABSTRACT

A new and distinct cultivar of poinsettia plant named 'Fissonosa', characterized by its bright pink bract color, medium sized but strongly lobed bracts, intense dark green and distinctly lobed foliage, compact and very well branched, but comparatively narrow plant habit, and its comparatively early flower response for a pink flower cultivar.

1 Drawing Sheet

The present invention relates to a new and distinct cultivar of poinsettia plant known by the cultivar name 'Fissonosa', and botanically known as *Euphorbia pulcherrima*. This plant will be marketed under the name "Fisson Pink" both in Europe and in the United States.

'Fissonosa' is a product of a mutation induction program carried out by the inventor, Katharina Zerr, in Hillscheid, Germany, in 1994. The primary objective of the induction program was to expand the bract color ranges of Fisson, disclosed in U.S. Plant Pat. No. 9,365, and characterized by its bright red bracts with pointed lobes, dark green foliage and compact habit.

The irradiation program comprised exposing rooted cuttings taken from plants of the parent cultivar to an X-ray source of 30 Gy dosage in Ahrensburg, Germany, under the supervision of the inventor.

The irradiated plants were grown out in a greenhouse in Hillscheid, Germany, and were asexually propagated by the inventor by taking cuttings. The plants resulting from these cuttings were screened for mutations as small flowering single stem plants in autumn 1994. The mutations discovered were identified by numbers. Parts of plants showing a positive mutation were left to develop vegetative shoots which were used as cuttings and grown out.

'Fissonosa' is based on a clone obtained by asexual reproduction performed by or under the supervision of the inventor in Hillscheid, Germany, with the clone being derived from a single plant with a ring of bracts completely turned pink. Subsequent asexual propagation and selection by or under the supervision of the inventor developed a uniform clone with pink bracts. The clone was examined and compared to other clones in a trial cultivation in summer 1995 and, on a larger scale, in autumn 1995. Horticultural examination has confirmed that the combination of characteristics disclosed for 'Fissonosa' are firmly fixed and are retained through successive generations of asexual reproduction.

The following traits have been repeatedly observed and are determined to be basic characteristics of 'Fissonosa' which in combination distinguish this poinsettia as a new and distinct cultivar:

1. Bright pink bract color.
2. Flat involucre with strongly lobed, medium sized bracts.
3. Intense dark green foliage, distinctly lobed.

4. Compact and very well branched, but comparatively narrow plant habit.
5. Generally medium early flowering response, but comparatively early for a pink flowered variety.

'Fissonosa' has not been observed under all possible environmental conditions. The phenotype may vary significantly with variations in environment such as temperature, light intensity, and daylength without, however, any variance in genotype. The following observations, measurements and comparisons describe plants grown in Hillscheid, Germany, under greenhouse conditions which approximate those generally used in commercial practice.

The plants described were planted as rooted cuttings in 12 cm pots on August 24, pinched 14 days later, and grown at 20° C. minimum day and night temperature. The plants initiated flowers in natural short day conditions in autumn. Observations and measurements were taken mainly at the beginning of flowering.

Of the many commercial cultivars known to the inventor, the most similar in comparison to 'Fissonosa' are the parent cultivar 'Fisson' and the commercial cultivars 'Lilo Pink' and 'Freedom Pink'.

In contrast to the bright red bracts of the parent cultivar 'Fissonosa', has pink colored bracts, and light brownish-pink colored petioles. 'Fissonosa' is very close to the parent in other morphological characteristics.

In comparison to 'Lilo Pink', 'Fissonosa' has a similar shade of pink bract color, but differently shaped bracts, and leaves with stronger lobes. Pinched plants of 'Fissonosa' are much better branched. The flower response of 'Fissonosa' is not quite as early as 'Lilo Pink', but the retention of the cyathia is better.

In comparison to 'Freedom Pink', 'Fissonosa' has smaller bracts with a smooth surface and stronger lobed shape. Flower response of 'Fissonosa' is somewhat later, while retention of the cyathia is better.

The accompanying color photographic drawing shows typical inflorescence and foliage of 'Fissonosa', with colors being as true as possible with illustrations of this type. The photograph shows a typical mature potted plant.

In the following description, color references are made to The Royal Horticultural Society Colour Chart. The color values were determined indoors in a north light.

Classification:

*Botanical.—Euphorbia pulcherrima.*

*Commercial.*—Poinsettia, cv. 'Fissonosa'.

Parentage: Induced mutation of 'Fisson'.

Plant Description:

*Form.*—Compact and well branched; pinched plants are bushy, but not very broad.

*Growth habit.*—Weak to medium growth. Height (above soil line): 20 cm. Diameter/width: 42 cm. Average no. of branches: 7.4.

*Rooting.*—Medium (20–24 days).

*Blooming habit.*—Flowering begins under natural short day conditions in late November; response time is approximately 9 weeks; plant is saleable about 1 week before the cyathia open.

*Foliage.*—Size: Leaf blade: Length: 13.5 cm. Width: 9.5 cm (lobed leaf). Petiole: 5.0 cm. Color: Generally dark green. Upper surface: about 139 A. Under surface: about 137 B. Leaf petiole: Brownish pink, about 179 B-C. Shape: Roughly triangular, strong lobes, wedge-shaped base; smaller leaves without lobes are broad elliptical. Texture: Surface smooth and flat. Edge of margin: Entire.

Flowering description:

*Cyathia.*—Few, 10–14, in a narrow cluster; retention is medium.

*Bracts, shape.*—Larger bracts are roughly. triangular, with strong lobes and wedge-shaped base, flat. Size: Largest bract is 13.5 cm, including petiole. Color: Generally bright pink. Color in the middle of the involucre is about 52 B. Primary bracts are lighter, about 51 B-C, and the smallest bracts are about 52 A. Aspect: Horizontal.

Reproductive organs:

*Nectar cups.*—Small to medium sized, yellow.

*Stamens.*—Reddish filaments.

*Pollen.*—Yellow, plenty.

*Styles.*—Reddish pink, 6-lobed stigma.

*Ovaries.*—Light to medium green, top light red, triangular, 3-celled, 3 ovules.

It is claimed:

1. A new and distinct cultivar of poinsettia plant named 'Fissonosa', as illustrated and described.

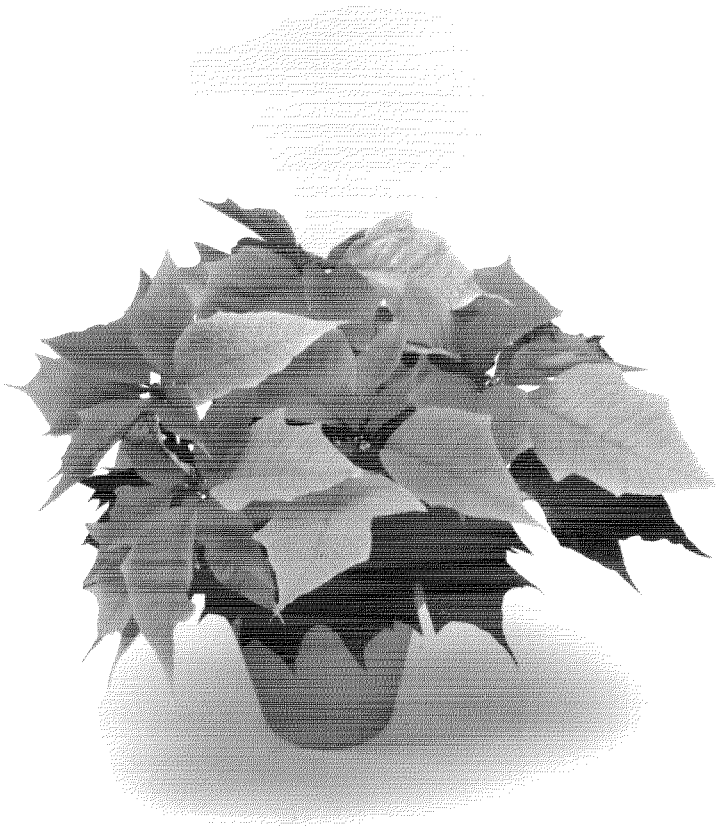

* * * * *